(12) United States Patent
Campbell et al.

(10) Patent No.: US 7,465,928 B2
(45) Date of Patent: Dec. 16, 2008

(54) APPARATUS AND METHODS FOR GUIDING CABLES AROUND A ROTATING GANTRY OF A NUCLEAR MEDICINE CAMERA

(75) Inventors: Michael Robert Campbell, Hoffman Estates, IL (US); Edward Zakrzewski, Carol Stream, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 53 days.

(21) Appl. No.: 11/528,108

(22) Filed: Sep. 27, 2006

(65) Prior Publication Data

US 2007/0069137 A1    Mar. 29, 2007

Related U.S. Application Data

(60) Provisional application No. 60/721,766, filed on Sep. 29, 2005.

(51) Int. Cl.
G01T 1/166 (2006.01)
G01T 1/161 (2006.01)
G01T 1/164 (2006.01)

(52) U.S. Cl. .............. 250/363.04; 250/363.02

(58) Field of Classification Search ............ 250/363.02, 250/363.04, 363.05, 363.08, 369; 378/20, 378/194, 198
See application file for complete search history.

(56) References Cited

U.S. PATENT DOCUMENTS

| | | | | |
|---|---|---|---|---|
| 4,099,061 A | * | 7/1978 | Zink et al. ............ | 378/4 |
| 4,366,577 A | * | 12/1982 | Brandt ............ | 378/194 |
| 5,097,132 A | * | 3/1992 | Plummer ............ | 250/363.08 |
| 6,364,526 B2 | * | 4/2002 | Ivan et al. ............ | 378/198 |
| 6,718,003 B2 | * | 4/2004 | Sasaki ............ | 378/4 |
| 2004/0061078 A1 | * | 4/2004 | Muramatsu et al. ...... | 250/492.3 |

* cited by examiner

*Primary Examiner*—David P Porta
*Assistant Examiner*—Faye Boosalis
(74) *Attorney, Agent, or Firm*—Peter L. Kendall

(57) ABSTRACT

An apparatus for guiding cables around a rotating gantry which includes a guide chain having a first end and a second end, wherein the first end is connected to a stationary portion of the rotating gantry and the second end is connected to a rotating portion of the gantry. The apparatus for guiding cables around a rotating gantry also includes means for maintaining the guide chain adjacent to at least one of the stationary portion and the rotating portion of the rotating gantry. Specifically, the means for maintaining the guide chain adjacent to at least one of the stationary portion and the rotating portion of the rotating gantry includes a plurality of plates connected to the guide chain and a magnetic strip positioned adjacent to at least one of the stationary portion and the rotating portion of the rotating gantry. The plurality of plates is preferably formed of a ferrous metal. In the apparatus for guiding cables around a rotating gantry, the magnetic strip may be connected adjacent to an inner diameter of the stationery portion of the rotating gantry, or any other suitable surface.

25 Claims, 5 Drawing Sheets

APPARATUS AND METHODS FOR GUIDING CABLES AROUND A ROTATING GANTRY OF A NUCLEAR MEDICINE CAMERA

CROSS-REFERENCE TO RELATED APPLICATION AND CLAIM FOR PRIORITY

This application claims priority under 35 U.S.C. § 119(e) from copending provisional application Ser. No. 60/721,766 filed Sep. 29, 2005.

BACKGROUND OF THE INVENTION

1. Technical Field

The present invention relates to gantry systems, and more particularly to apparatus and methods for guiding cables around a rotating gantry of a nuclear medicine camera apparatus.

2. Discussion of Related Art

Medical diagnostic imaging began with the discovery of x-rays by W. C. Roentgen in 1895 and today includes radiography, nuclear medicine imaging, ultrasound imaging, computed tomographic imaging, and magnetic resonance imaging. In general, the goal of each type of medical imaging is to provide a spatial mapping of a parameter, feature, or biological process within a patient.

In radiology and computed tomography, a source of x-rays is transmitted through the patient onto a suitable detector such as a film or a plate. The detector measures the intensity distribution of the incident beam of x-rays and provides an image representing the attenuation of the radiation resulting from the absorption and scattering within the patient's body.

Nuclear medicine involves injection of a radiopharmaceutical into a patient and measurement of the intensity distribution of gamma radiation emitted from the patient's body. Radiopharmaceuticals are formed by attaching a radioactive tracer to a pharmaceutical that is known to preferentially accumulate in the organ of interest. Thus, the radiation pattern is a measure of blood flow, metabolism, or receptor density within the organ of interest and provides information about the function of the organ. Either a single projection image of the radiation pattern may be taken (planar imaging) or many projection images may be acquired from different directions and used to compute the three dimensional emission distribution (single photon emission computed tomography, or SPECT). Radiation-imaging systems used in nuclear medicine are often referred to as "gamma" cameras because emitted gamma photons are detected by the system.

Nuclear or gamma cameras have included a detector head which receives radiation emanating from the patient. The detector head includes a flat scintillation crystal which converts incident radiation to flashes of light. Internal electronics convert each flash of light into an electric signal indicative of the location and energy of the received incident radiation event. Collimators are commonly mounted on the face of the detector head such that the scintillation crystal only receives radiation coming generally straight toward it. Generally, the collimators are a series of lead vanes arranged in a grid pattern. The height of the vanes and their spacing control the angle at which received radiation may differ from perpendicular. Different collimators are provided for different types of medical procedures.

Various mechanical gantry systems are known in the art. Many of the known gantry systems enable the detector head, typically on the order of several hundred pounds, to be positioned at a selected location over the patient. Commonly, the gantry is also motor-controlled such that the detector head can be moved continuously or intermittently either (i) longitudinally along the length of the patient or (ii) circumferentially around the patient. Some gantry systems also support a second detector head which is positioned diametrically opposed, around the patient, from the first detector head.

For axial scans, the camera head and the patient are moved relative to each other. In some of the prior art systems, the entire camera gantry was mounted on floor rails to be moved longitudinally relative to a stationary patient. Other prior art gantry systems are mounted on rails to move relative to a stationary patient. Typically, these gantry systems are supported on three or four wheels.

One of the design challenges in a nuclear medicine camera is how to guide the electrical cables from the stationary outer structure of the system to the rotating gantry and detectors, which typically have approximately 1.5 revolutions of travel as they rotate around the patient. The method used on the Siemens E.CAM system, for example, is to wrap the cables one way around the rotating inner diameter, then unwind and wrap the cables the other way around the same diameter as the detector head rotates in the opposite direction. As the cable is unwrapped, approximately seven (7) feet of slack must be taken up by a system of pulleys and a sliding spring-loaded accumulator/tensioner wheel. Methods of this type, while effective, tend to require a relatively large number of moving parts and thus can be expensive to manufacture and maintain. Plastic cable guide type chains are cost effective and are commonly used to guide cables on moving systems. However, since the chain would need to rotate all the way around the gantry ring, it would need a support system to resist falling for most of its travel.

Another challenge is how to individually sense both ends of travel for a rotary axis with approximately 1.5 revolutions of motion. If limit switches are simply used to sense a flag on the rotating gantry, they will activate every time the flag goes by (once per 360 degree revolution of the camera), which would include "on" signals in the middle of a 540 degree range of travel. This method can be made to work, however, if the switch logic is processed at a high level by the machine control software. Using the system drive motor's servo-controlled position or even a separate encoder (or potentiometer, as with E.CAM) is another method, but this too relies on high level machine control software processing the signal to determine the ends of travel. A potentially more robust method would be to use a system with two limit switches that turn on only when the system is at each respective end of travel. Thus simple on/off logic could be used to always stop motion whenever a limit switch is activated.

The present invention contemplates a new and improved gantry system which overcomes the above-referenced problems and others.

SUMMARY OF THE INVENTION

In accordance with one aspect of the present invention, the cables are contained and guided by a plastic chain that is held in place by clipped-on metal plates as it moves by a magnetic surface. The plastic chain also provides a method to sense both ends of travel for the rotating gantry through a 540 degree range of motion.

Accordingly, the invention provides an apparatus for guiding cables around a rotating gantry which includes a guide chain having a first end and a second end, wherein the first end is connected to a stationary portion of the rotating gantry and the second end is connected to a rotating portion of the gantry. The apparatus for guiding cables around a rotating gantry also maintains the guide chain adjacent to at least one of the stationary portion and the rotating portion of the rotating gantry. Specifically, a number of plates connected to the guide chain maintain the guide chain adjacent to at least one of the stationary portion and the rotating portion of the rotating gantry in conjunction with a magnetic strip positioned adjacent to at least one of the stationary portion and the rotating portion of the rotating gantry. The plurality of plates is preferably formed of a ferrous metal. In the apparatus for guiding cables around a rotating gantry, the magnetic strip may be connected adjacent to an inner diameter of the stationery portion of the rotating gantry, or any other suitable surface.

The transfer loop portion of the guide chain is configured to travel approximately 310 degrees. The transfer loop portion of the guide chain is the section of the chain that between the stationary portion and the rotating portion of the gantry. Accordingly, the apparatus for guiding cables around a rotating gantry in accordance with the present invention further includes at least one limit switch mounted on the stationary portion of the rotating gantry, wherein the at least one limit switch is configured to sense a side of the guide chain. Preferably, two limit switches are mounted on the stationary portion of the rotating gantry at a location corresponding to the point at which the transfer loop portion of the guide chain travels approximately 310 degrees as the rotating gantry travels from one end of its range of motion to the other end of its range of motion.

According to another aspect of the invention, a nuclear medicine camera system is provided including a rotating gantry mounted for horizontal translating movement along a horizontal path; at least one detector head mounted on the gantry; a patient table assembly rigidly mounted at opposite ends to first and second pedestals, wherein the patient table is configured to pass through a central aperture formed by the movable gantry; a guide chain having a first end and a second end, wherein the first end is connected to a stationary portion of the rotating gantry and the second end is connected to a rotating portion of the gantry; and means for maintaining the guide chain adjacent to at least one of the stationary portion and the rotating portion of the rotating gantry. Specifically, the means for maintaining the guide chain adjacent to at least one of the stationary portion and the rotating portion of the rotating gantry includes a plurality of plates connected to the guide chain and a magnetic strip positioned adjacent to at least one of the stationary portion and the rotating portion of the rotating gantry.

According to a still further aspect of the invention, a retaining mechanism is provided for a rotating gantry, wherein the retaining mechanism maintains a guide chain around the rotating gantry. The retaining mechanism includes a plurality of plates connected to the guide chain and a magnetic strip positioned adjacent to at least one of a stationary portion and a rotating portion of the rotating gantry. The plurality of plates connected to the guide chain is formed of metal and the magnetic strip is connected adjacent to an inner diameter of the stationery portion of the rotating gantry. Preferably, the retaining mechanism further includes at least one limit switch mounted on the stationary portion of the rotating gantry, wherein the at least one limit switch is configured to sense a side of the guide chain.

BRIEF DESCRIPTION OF THE DRAWINGS

The accompanying drawings, which are incorporated in and constitute a part of this specification, illustrate exemplary embodiments of the invention and, together with a general description of the disclosure given above, and the detailed description of the embodiments given below, serve to explain the principles of the invention.

DETAILED DESCRIPTION OF PREFERRED EMBODIMENTS

Figure 1:
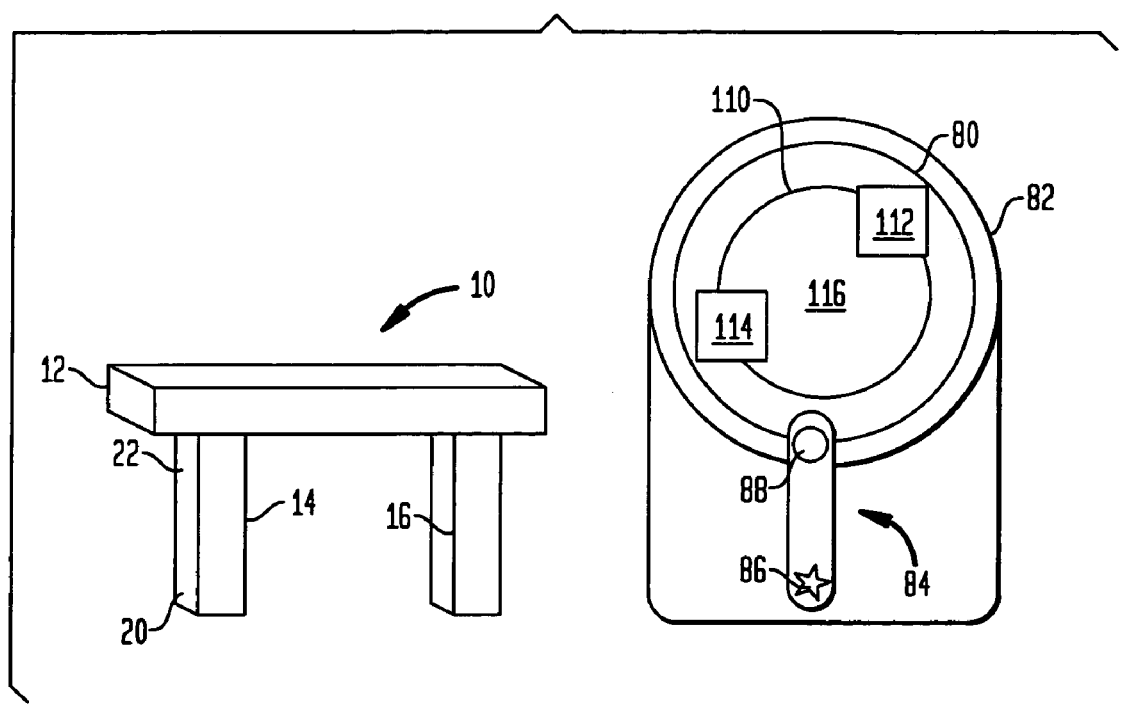
FIG. 1 is a perspective view of a gamma camera gantry and patient support table for use with the apparatus and methods for guiding cables around a rotating gantry in accordance with the present invention.

Preferred embodiments of the presently disclosed apparatus and method for guiding cables around a rotating gantry of a nuclear medicine camera will now be described in detail with reference to the figures, in which like reference numerals identify corresponding elements throughout the several views.

With reference to FIG. 1, a patient table assembly 10 includes a top or patient support 12 and a pair of end vertical supports or pedestals 14, 16 which are fixedly mounted to the floor. The top is fixed at each end to one of the pedestals. The first and second supports each include a floor mounted portion 20 in which a top supporting portion 22 is telescopically received. A drive motor and threaded screw may be used to selectively raise and lower the top supporting portion. The drive motors (not shown) of both the head and foot end supports 14, 16 are electrically connected together such that both ends of the table are always raised and lowered concurrently.

With continued reference to FIG. 1, an outer gantry 80 is movably mounted on tracks 82 which extend parallel to the longitudinal axis of the gantry. An outer gantry moving means 84 selectively moves the outer gantry 80 along the tracks 82 in a path parallel to the longitudinal axis of the table assembly 10. In the illustrated embodiment, the longitudinal moving means includes a motor 86, which selectively drives a wheel 88 that frictionally engages the tracks 82 and drives the gantry 80 therealong.

With reference again to FIG. 1, an inner or rotating gantry 110 is rotatably mounted on the outer gantry 80. A first camera or detector head 112 is movably mounted on the inner gantry. A second detector head 114 is movably mounted on the inner gantry opposite to the first camera head. The inner gantry defines a central, patient receiving aperture 116 for receiving the patient table top 12 and a supported patient along the longitudinal axis. The aperture 116 is enlarged to receive the detector heads in any of a variety of displacements from the longitudinal axis and any of a variety of angular orientations to the axis.

Figure 2:
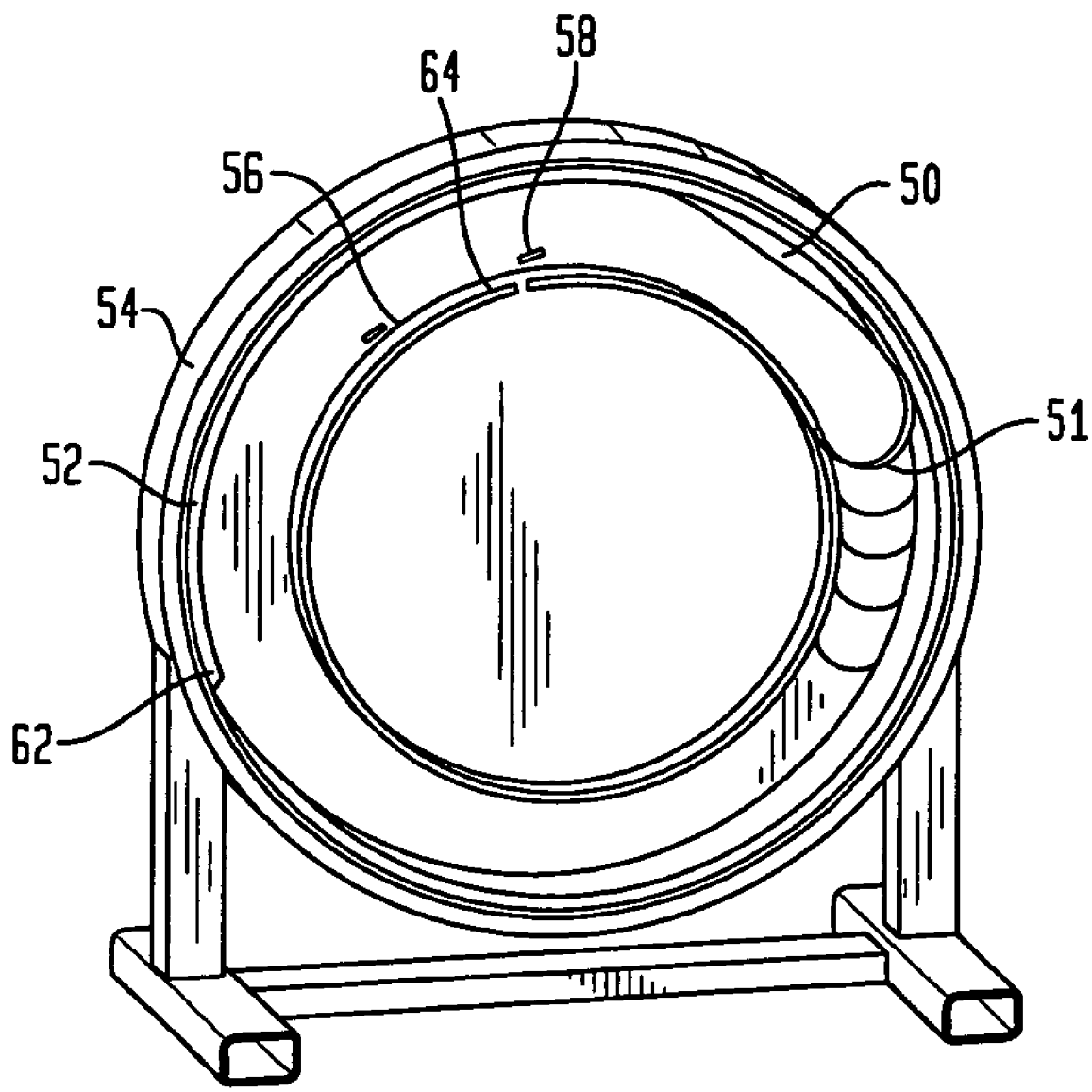
FIG. 2 is a perspective view of a gamma camera gantry having an apparatus for guiding cables around a rotating gantry in accordance with the present invention.

Referring now to FIG. 2, there is shown a perspective view of a gantry system having an apparatus for guiding cables around a rotating gantry in accordance with the present invention. There are many cables that must be routed to the rotating gantry of a nuclear medicine camera. Typically, at least one cable is required to transmit each of the following signals: detector power, detector data, motion power, and motion data. To facilitate routing these cables, as well as any other cables that may exist, from the stationary outer structure of the camera to the rotating gantry, the cables are routed inside a plastic cable carrier type chain 50. The chain 50 is located inside the rotating inner ring 52 of the gantry ring gear 54. A first end 62 of the chain 50 is attached to the inner ring and thus rotates with it through 540 degrees of motion. The second end 64 of the chain 50 does not rotate and is mounted to the stationary structure surrounding the center bore of the camera. As the ring 52 rotates, the chain 50 will be pulled from the inner ring's inside diameter to the stationary portion of the gantry, where a transferring loop portion 51 of the chain 50 between the rotating and stationary portions of the gantry moves as the ring rotates. Examples of prior art cable guide chains are manufactured by Igus Industries and are disclosed in U.S. Pat. Nos. 6,745,555 and 6,425,238, and all are incorporated by reference herein. The exact configuration of the cable chain may vary. Accordingly, it is contemplated that any suitable chain configuration known to one having ordinary skill in the art may be used in conjunction with the present invention.

Figure 3:
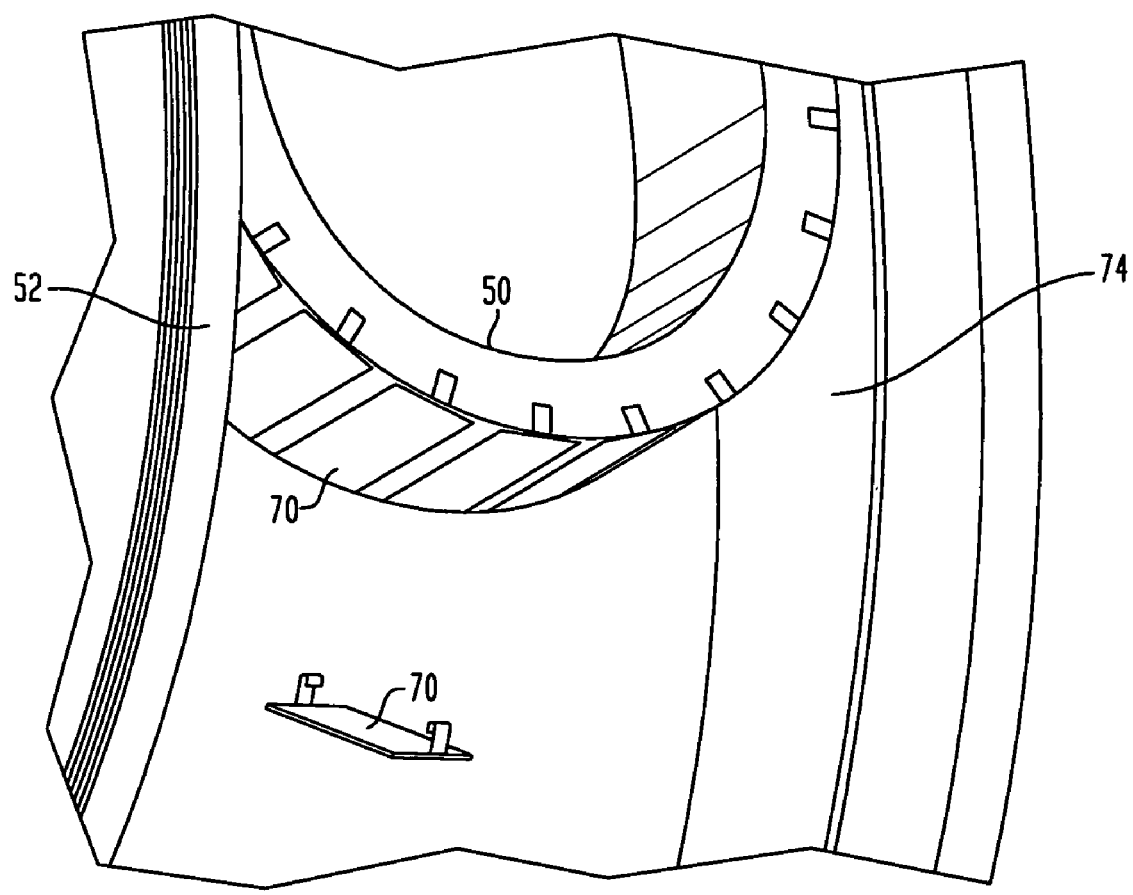
FIG. 3 is a detail view of a magnetic attraction system in accordance with the present invention.

Referring now to FIG. 3, a retaining mechanism in accordance with the present invention is illustrated. The retaining mechanism utilizes a magnetic attraction system to prevent the chain 50 from falling away from the ring 52 as the gantry rotates. The magnetic attraction system utilizes an adhesive backed strip magnet 74 that has been applied to the inside diameter of the inner ring 52. Steel backing plates 70 are attached to the plastic chain links of chain 50 such that each plate 70 may be held by the strip magnet 74. The steel plates 70 can be placed on every link or every other link, depending on the weight of the chain/cable assembly and how much attraction force is required to hold the chain 50 in place adjacent to ring 52. A plurality of possible methods of attachment between the steel plates and the plastic links exist, including but not limited to, clip-on, glue, screws, insert molding, etc. The plates 70 are preferably formed of a ferrous material. As the ring 52 continues to rotate, a portion of the chain 50 will also be pulled across the bottom of the stationary bore structure's outside diameter (OD). The strip magnet 74 may also be applied to the outer surface of ring 52 to further hold the chain 50 from falling away from the outer surface of ring 52.

Figure 4:
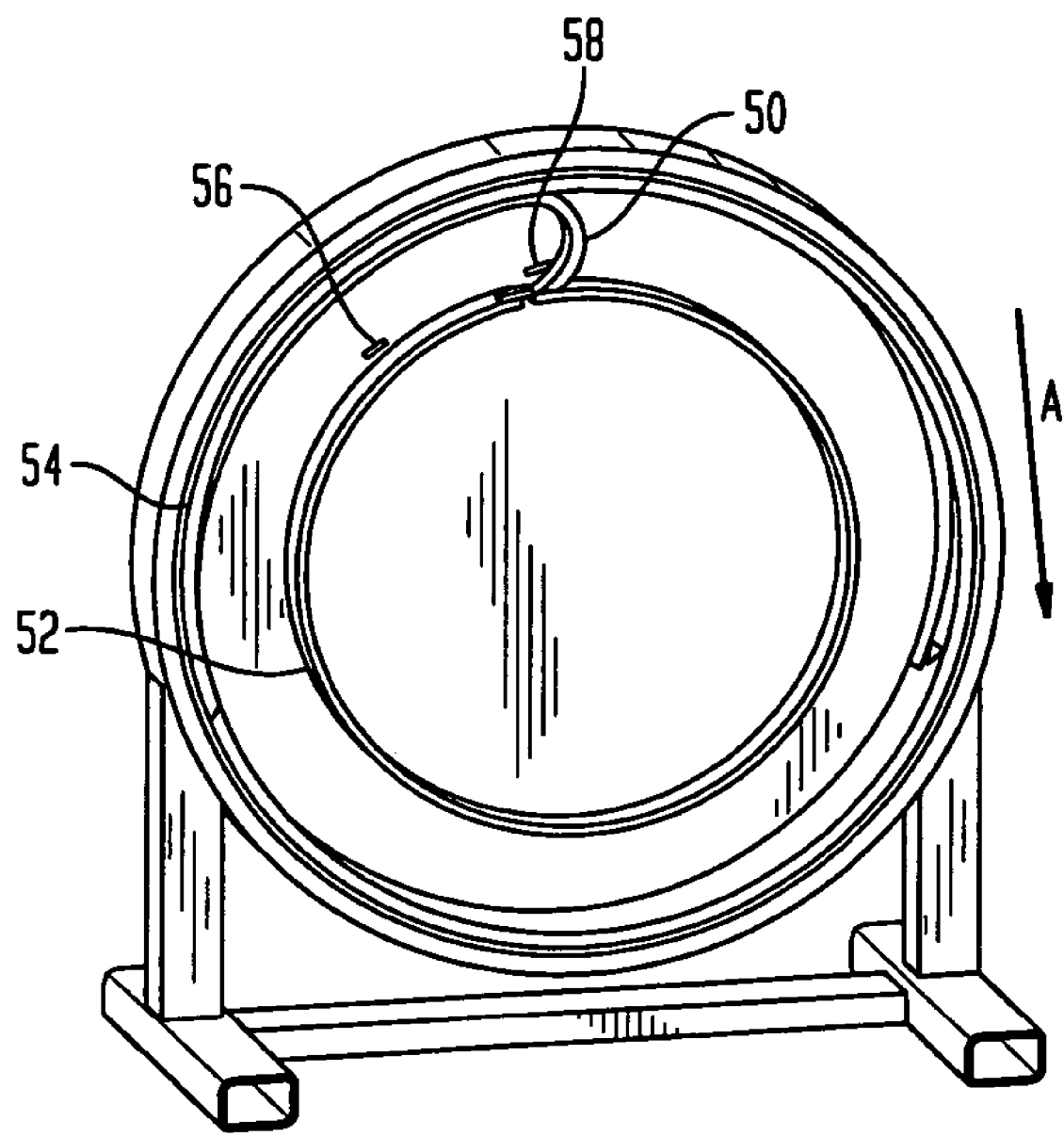
FIG. 4 is a perspective view of a gamma camera gantry having an apparatus for guiding cables around a rotating gantry in accordance with the present invention.
Figure 5:
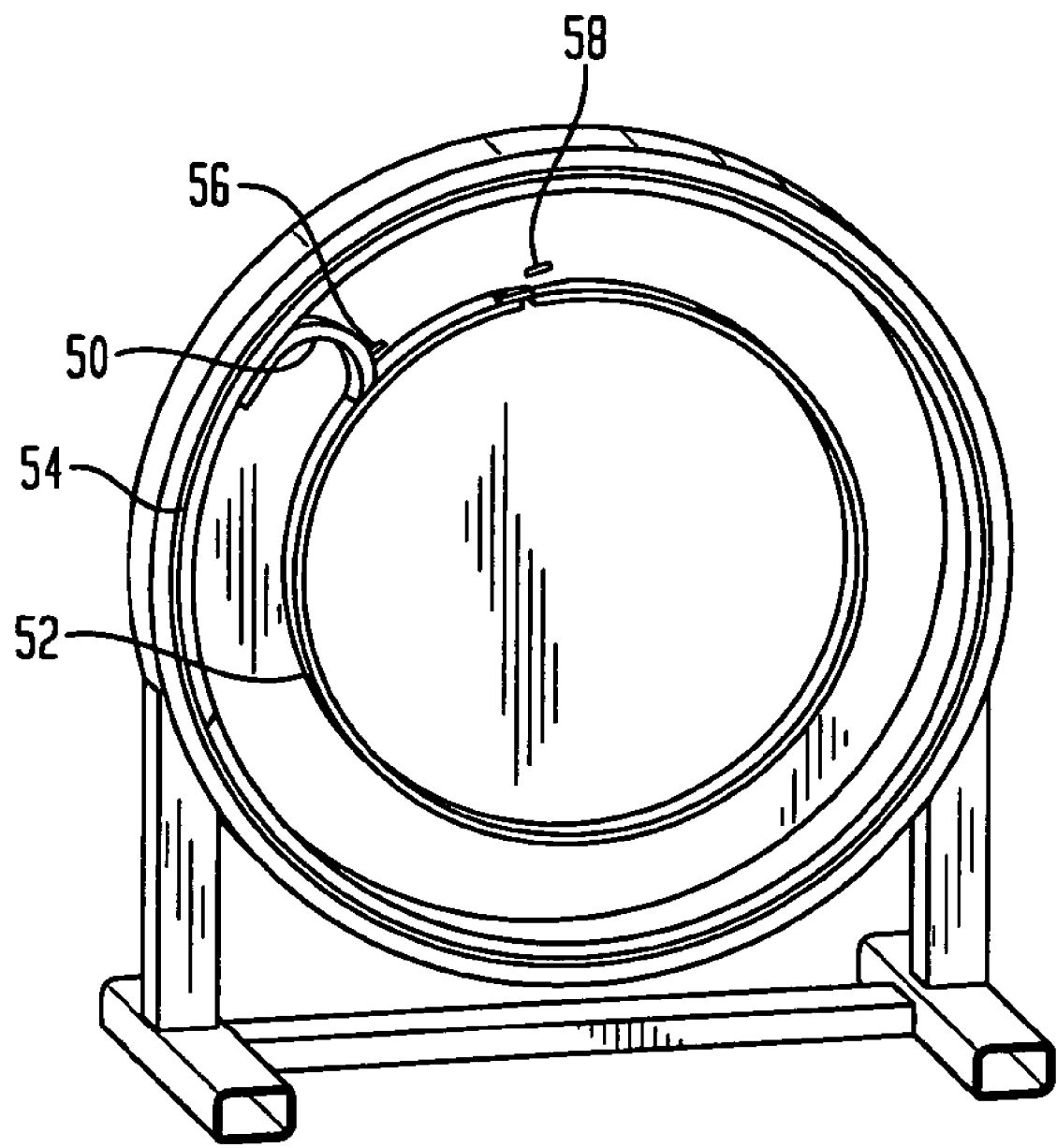
FIG. 5 is a perspective view of a gamma camera gantry having an apparatus for guiding cables around a rotating gantry in accordance with the present invention.

As the gantry rotates clockwise (CW) in the direction of arrow A illustrated in FIG. 4 from the counter-clockwise (CCW) end of travel toward the CW end of travel, the chain 50 is transferred away from the inside diameter of rotating ring 54 and wrapped around the stationary bore structure 52 outside diameter. As this transfer occurs and the ring rotates through 540 degrees of motion, the transferring loop portion of the chain rotates through approximately 310 degrees of motion (see FIGS. 4 and 5). A reflective type optical limit switch 56, 58 is mounted at each end of this 310 degree motion, sensing the side of the loop. Since the loop travel is less than one full revolution, each switch 56, 58 is only able to activate when the chain 50 is at its respective end of travel with no additional "on" signals in the middle of travel. Thus simple, robust on/off logic can be used to always stop motion if/when either limit switch 56, 58 is activated.

It will be understood that various modifications may be made to the embodiments disclosed herein. For example, although the above embodiments are described with reference to nuclear or gamma cameras, it is contemplated that the disclosure is not limited to such an application and may be applied to gantry systems for various medical diagnostic equipment. Additionally, although the mechanism is described with particular reference to nuclear or gamma camera systems, it is contemplated that the invention will also find application in conjunction with PET and other diagnostic equipment.

The invention claimed is:

1. Apparatus for guiding cables around a rotating gantry comprising:
    a guide chain containing cables and having a first end and a second end, wherein the first end is connected to a stationary portion of the rotating gantry and the second end is connected to a rotating portion of the gantry, which stationary and rotating portions are concentrically located with respect to each other; and
    a retention mechanism that retains the guide chain against an outer one of the stationary portion and the rotating portion of the rotating gantry, wherein the retention mechanism comprises a plurality of plates connected to the guide chain, and a magnetic strip positioned adjacent to an outer one of the stationary portion and the rotating portion of the rotating gantry for magnetically attracting said plates.

2. The apparatus for guiding cables around a rotating gantry as recited in claim 1 wherein the plurality of plates connected to the guide chain are formed of metal.

3. The apparatus for guiding cables around a rotating gantry as recited in claim 1 wherein rotating portion of said gantry is concentrically located outside said stationary portion, and the magnetic strip is connected adjacent to an inner diameter of the rotating portion of the rotating gantry.

4. The apparatus for guiding cables around a rotating gantry as recited in claim 1 wherein a transferring loop portion of the guide chain between said stationary and rotating portions of the rotating gantry is configured to travel approximately 310 degrees as the rotating gantry travels approximately 540 degrees.

5. The apparatus for guiding cables around a rotating gantry as recited in claim 4 further comprising at least one limit switch mounted on the stationary portion of the rotating gantry, wherein the at least one limit switch is configured to sense a side of the guide chain.

6. The apparatus for guiding cables around a rotating gantry as recited in claim 4 further comprising two limit switches mounted on the stationary portion of the rotating gantry.

7. The apparatus for guiding cables around a rotating gantry as recited in claim 6 wherein each of the two limit switches is mounted at a location corresponding to the point at which said transferring loop portion of the guide chain travels approximately 310 degrees from one end of a range of motion of said rotating gantry to the other.

8. A nuclear camera system comprising:
    a rotating gantry mounted for horizontal translating movement along a horizontal path;
    at least one detector head mounted on said gantry;
    a patient table assembly rigidly mounted at opposite ends to first and second pedestals, wherein the patient table is configured to pass through a central aperture formed by the rotating gantry;
    a guide chain having a first end and a second end and containing a cable connectable to said detector head, wherein the first end is connected to a stationary portion of the rotating gantry and the second end is connected to a rotating portion of the gantry, wherein said stationary and rotating portions are concentrically located with respect to each other; and
    a retention mechanism that retains the guide chain against an outer one of the stationary portion and the rotating portion of the rotating gantry, wherein the retention mechanism comprises a plurality of plates connected to the guide chain, and a magnetic strip positioned adjacent to at least one of the stationary portion and the rotating portion of the rotating gantry.

9. The nuclear camera system as recited in claim 8 wherein the plurality of plates connected to the guide chain are formed of metal.

10. The nuclear camera system as recited in claim 8 wherein the rotating portion of said gantry is concentrically located outside said stationary portion and magnetic strip is connected adjacent to an inner diameter of the rotating portion of the rotating gantry.

11. The nuclear camera system as recited in claim 8 wherein a transferring loop portion of the guide chain between said stationary and rotating portions of the rotating gantry is configured to travel approximately 310 degrees as the rotating gantry travels approximately 540 degrees.

12. The nuclear camera system as recited in claim 11 further comprising at least one limit switch mounted on the stationary portion of the rotating gantry, wherein the at least one limit switch is configured to sense a side of the guide chain.

13. The nuclear camera system as recited in claim 11 further comprising two limit switches mounted on the stationary portion of the rotating gantry.

14. The nuclear camera system as recited in claim 13 wherein each of the two limit switches is mounted at a location corresponding to the point at which said transferring loop portion of the guide chain travels approximately 310 degrees from one end of a range of motion of said rotating gantry to the other.

15. A retaining mechanism provided on a rotating gantry having concentrically located stationary and rotating portions, the retaining mechanism being positioned to retain a guide chain against an outer one of the stationary and rotating portions of the rotating gantry, the retaining mechanism comprising:
 a plurality of plates connected to the guide chain; and
 a magnetic strip positioned adjacent to an outer one of said a stationary and rotating portions of the rotating gantry.

16. The retaining mechanism as recited in claim 15, wherein the plurality of plates connected to the guide chain are formed of metal.

17. The retaining mechanism as recited in claim 15, wherein the magnetic strip is connected adjacent to an inner diameter of the rotating portion of the rotating gantry.

18. The retaining mechanism as recited in claim 15, further comprising at least one limit switch mounted on the stationary portion of the rotating gantry, wherein the at least one limit switch is configured to sense a side of the guide chain.

19. A method for containing and guiding the cables of a nuclear medicine camera around a rotating gantry having concentrically located stationary and rotating portions, comprising the steps of:
 encasing the cables in a guide chain;
 attaching the first end of the guide chain to a stationary portion of the gantry;
 attaching the second end of the guide chain to a rotating portion of the gantry; and
 retaining the guide chain against an outer one of said stationary and rotating portions,
 wherein the step of retaining further comprises providing at least one magnetically attractive plate to a link of said chain, providing a magnetic strip to at least one of said stationary portion and rotating portion of said gantry, and maintaining the guide chain adjacent to at least one of the stationary portion and the rotation portion of the gantry through use of said magnetic strip and plurality of plates.

20. The method of claim 19, further comprising connecting a plurality of plates to the guide chain.

21. The method of claim 20, wherein the plates connected to the guide chain are formed of metal.

22. The method of claim 20, further comprising connecting the magnetic strip to an inner diameter of the rotating portion of the rotating gantry.

23. The method of claim 19, further comprising configuring the guide chain such that a transferring loop portion thereof between said stationary and rotating gantry portions travels approximately 310 degrees as the rotating gantry travels approximately 540 degrees.

24. The method of claim 19, further comprising mounting at least one limit switch on the stationary portion of the rotating gantry, wherein the at least one limit switch is configured to sense a side of the guide chain.

25. The method of claim 24, wherein the at least one limit switch is mounted at a location corresponding to the point at which said transferring loop portion of the guide chain travels approximately 310 degrees from one end of a range of motion of said rotating gantry to the other.

* * * * *